United States Patent [19]

Meier et al.

[11] Patent Number: 5,376,290
[45] Date of Patent: Dec. 27, 1994

[54] SUBSTITUTED PHENOLS AS STABILIZERS

[75] Inventors: Hans R. Meier; Samuel Evans; Paul Dubs, all of Marly, Switzerland

[73] Assignee: Ciba-Geigy Corporation, Ardsley, N.Y.

[21] Appl. No.: 781,637

[22] Filed: Oct. 18, 1991

Related U.S. Application Data

[60] Division of Ser. No. 136,686, Dec. 22, 1987, abandoned, and a continuation of Ser. No. 578,926, Sep. 6, 1990, abandoned.

[30] Foreign Application Priority Data

Dec. 24, 1986 [CH] Switzerland ............... 5235/86

[51] Int. Cl.$^5$ ................. C10M 135/24; C10M 135/20
[52] U.S. Cl. ..................... 252/47.5; 252/48.2; 252/48.4; 252/48.6; 252/404; 568/41; 568/44; 568/46; 568/48
[58] Field of Search ............... 252/47.5, 48.2, 48.4, 252/48.6

[56] References Cited

U.S. PATENT DOCUMENTS

| | | | |
|---|---|---|---|
| 2,415,833 | 2/1947 | Mikeska et al. | 252/42.6 |
| 2,417,118 | 3/1947 | McCleary et al. | 260/609 |
| 3,227,677 | 1/1966 | Simpson | 524/289 |
| 3,553,270 | 1/1971 | Wallensak et al. | 260/609 |
| 3,660,352 | 5/1972 | Song | 252/48.2 |
| 3,772,390 | 11/1973 | Song | 252/48.2 |
| 4,021,468 | 5/1977 | Lind | 260/470 |
| 4,091,037 | 5/1978 | Arold | 260/609 |
| 4,108,831 | 8/1978 | Cottman | 260/45.95 |
| 4,358,616 | 11/1982 | Wedemeyer et al. | 568/45 |
| 4,551,259 | 11/1985 | Braid | 252/48.2 |
| 4,707,300 | 11/1987 | Sturm et al. | 252/404 |
| 4,741,846 | 5/1988 | Evans | 252/48.2 |
| 4,759,862 | 7/1988 | Meier | 252/475 |
| 4,772,405 | 9/1988 | Wirth | 252/48.2 |
| 4,820,756 | 4/1989 | Pitteloud et al. | 524/289 |
| 4,857,572 | 8/1989 | Meier et al. | 252/48.2 |
| 4,874,885 | 10/1989 | Stegmann et al. | 560/15 |
| 4,946,610 | 8/1990 | Lam et al. | 252/48.2 |

FOREIGN PATENT DOCUMENTS 165209 12/1985 European Pat. Off. .
273013 6/1988 European Pat. Off. .

OTHER PUBLICATIONS

Chemical Abstract 86:5067n; Synthesis of New Organosulfur Derivatives of Shielded Phenols, Jan. 1977.
Chemical Abstract 89:27167j; Phenol Derivatives as Oil Stabilizers, Jul. 1978.
J. Am Chem. Soc. vol. 71 p. 2264 Jan. (1949).
Abdullaeva, Chem. Abstracts 83:79881h Sep. 1975.

Primary Examiner—Ellen M. McAvoy
Attorney, Agent, or Firm—JoAnn Villamizer; Luther A. R. Hall

[57] ABSTRACT

Novel compositions are described which comprise an elastomer or a lubricant and at least one compound of the formulae I or II

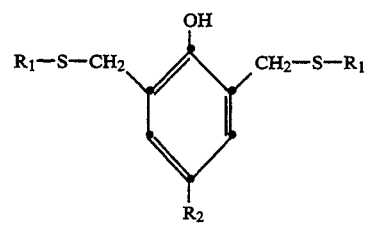

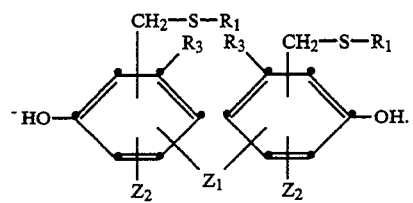

The symbols $R_1$, $R_2$, $R_3$, $Z_1$ and $Z_2$ are as defined in claim 1.

The compounds of the formula II and some of the compounds of the formula I are novel, and they are used especially as antioxidants.

12 Claims, No Drawings

SUBSTITUTED PHENOLS AS STABILIZERS

This is a divisional of application Ser. No. 136,686 filed on Dec. 22, 1987, now abandoned, and a continuation of application Ser. No. 578,926, filed Sep. 6, 1990, now abandoned.

The present invention relates to compositions comprising substituted bis-(mercaptomethyl)-phenols as stabilizers and to novel bis-(mercaptomethyl)-phenols.

Phenols containing mercaptomethyl are known as stabilizers. Thus, for example, several bis-(mercaptomethyl)-phenols are listed in U.S. Pat. No. 2,417,118, but without precise data on the substituted sites on the phenol. These phenols are suitable as additives for lubricants, especially in engine oils.

U.S. Pat. No. 3,227,667 has disclosed 2,6-bis-(alkoxycarbonylalkylenethiomethyl)-4-alkylphenols as antioxidants for polyolefins.

According to EP-A-0,165,209, 2,4-bis-(mercaptomethyl)-6-alkylphenols, for example, are suitable as stabilizers for organic polymers and lubricants.

Several specific 2,6-bis-(mercaptomethyl)-phenols are also known as intermediates, for example 2,6-bis-(ethylthiomethyl)-4-methylphenol (DE-A1-2,838,273), 2,6-bis-(butylthiomethyl)-4-methylphenol [I. W. Rudermann and E. M. Fettes, J. Am. Chem. Soc. 71 (1949), 2264] as well as 2,6-bis-(phenylthiomethyl)- and 2,6-bis-(benzylthiomethyl)-4-methylphenol [Abdullaeva, C. A. volume 83 (1975), 79881 h].

There is still a demand for effective stabilizers for materials which are sensitive to thermal, oxidative or light-induced degradation.

The invention therefore relates to a composition comprising an elastomer or a lubricant and at least one compound of the formulae I or/and II

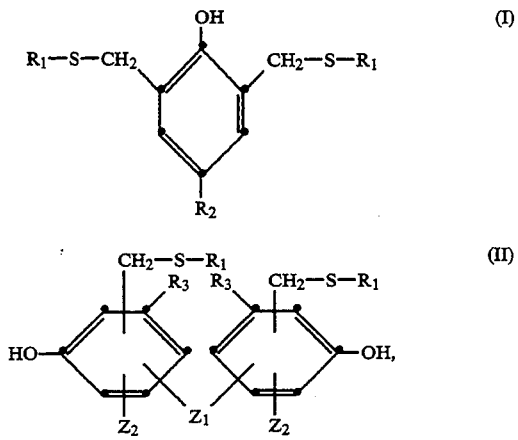

in which the radicals $R_1$ are identical or different and independently of one another are $C_1$-$C_{20}$-alkyl which is unsubstituted or substituted by 1 or 2 hydroxyl groups or/and interrupted by —O—, or are $C_1$-$C_4$-alkylene-COOR$_2$', $C_1$-$C_4$-alkylene-CO-NR$_2$"R$_4$, $C_5$-$C_{12}$-cycloalkyl, phenyl, 1-naphthyl, 2-naphthyl, $C_1$-$C_4$-alkylphenyl or phenyl-$C_1$-$C_4$-alkyl, $R_2$, $R_2'$ and $R_2''$ independently of one another are $C_1$-$C_{20}$-alkyl, allyl, methylallyl, propargyl, $C_5$-$C_{12}$-cycloalkyl, phenyl or benzyl, $R_3$ is hydrogen, $C_1$-$C_{20}$-alkyl, $C_2$-$C_{18}$-alkenyl or halogen, $R_4$ is hydrogen, $C_1$-$C_{20}$-alkyl or $C_2$-$C_{18}$-alkenyl, $Z_1$ is —S— or —C($Z_3$)($Z_4$)— and $Z_2$ is hydrogen, $C_1$-$C_{20}$-alkyl or —CH$_2$—S—R$_1$, $Z_3$ and $Z_4$ independently of one another being hydrogen or methyl, with the proviso that the phenols of the formula II are free of the —CH$_2$—S—R$_1$ functional group in the m-position relative to the OH group.

Examples of $C_1$-$C_{20}$-alkyl $R_1$, $R_2$, $R_2'$, $R_2''$, $R_3$, $R_4$ and $Z_2$ are methyl, ethyl, n-propyl, isopropyl, n-butyl, sec-butyl, t-butyl, n-pentyl, isopentyl, n-hexyl, 1,1-dimethylbutyl, n-heptyl, n-octyl, 2-ethylhexyl, n-nonyl, n-decyl, 1,1,3,3-tetramethylbutyl, 1,1,3,3-tetramethylhexyl, n-undecyl, n-dodecyl, 1,1,3,3,5,5-hexamethylhexyl, 2,2,4,6,6-pentamethylhept-4-yl, n-tetradecyl, n-hexadecyl, n-octadecyl or n-eicosyl.

$R_1$ is preferably straight-chain $C_8$-$C_{20}$-alkyl, especially $C_8$-$C_{12}$-alkyl, for example n-octyl, n-decyl or n-dodecyl.

$R_2$, $R_2'$ and $R_2''$ are preferably methyl ethyl or branched $C_3$-$C_{20}$-alkyl, for example isopropyl, t-butyl, t-amyl, 2-ethylhexyl, 1,1,3,3-tetramethylbutyl, 1,1,3,3-tetramethylhexyl or 1,1,3,3,5,5-hexamethylhexyl and especially methyl, t-butyl, 2-ethylhexyl and 1,1,3,3-tetramethylbutyl.

$C_1$-$C_{20}$-Alkyl $R_1$ substituted by one or two hydroxyl groups is, for example, hydroxymethyl, 2-hydroxyethyl, 2-hydroxypropyl, 2-hydroxybutyl, 2-hydroxyhexyl, 2-hydroxyoctyl, 2-hydroxydecyl, 2-hydroxydodecyl, 2-hydroxytetradecyl, 2-hydroxyhexadecyl, 2-hydroxyoctadecyl, 2-hydroxyeicosyl or 2,3-dihydroxypropyl. $C_1$-$C_4$-Hydroxyalkyl, for example 2-hydroxypropyl or 2,3-dihydroxypropyl and especially 2-hydroxyethyl are preferred.

Alkyl $R_1$ interrupted by —O— can have one or more, for example 1 to 6, and especially 1 or 2 —O— interruptions and is, for example, 3-oxapropyl, 3-oxabutyl, 3-oxapentyl, 3,6-dioxaheptyl, 3,6,9-trioxadecyl or 3,6,9,12,15,18-hexaoxanonadecyl.

$C_2$-$C_{18}$-Alkenyl $R_3$ and $R_4$ are, for example, vinyl, allyl, but-3-enyl, pent-4-enyl, hex-5-enyl, oct-7-enyl, dec-9-enyl, dodec-11-enyl or octadec-17-enyl. Vinyl or allyl are preferred.

$C_5$-$C_{12}$-Cycloalkyl $R_1$, $R_2$, $R_2'$ and $R_2''$ are, for example cyclopentyl, cyclohexyl, cycloheptyl, cyclooctyl, cyclononyl, cyclodecyl, cycloundecyl or cyclododecyl. $C_5$-$C_7$-Cycloalkyl, and very particularly cyclohexyl in the case of $R_1$, are preferred.

Phenyl $C_1$-$C_4$-alkyl $R_1$ is, for example, benzyl, phenylethyl, α-methylbenzyl or α,α-dimethylbenzyl. Benzyl is preferred.

$C_1$-$C_4$-Alkylphenyl $R_1$ can have, for example, 1 to 3, especially 1 or 2 alkyl groups and is, for example, o-, m- or p-tolyl, 2,4-, 2,6-, 3,5- or 3,6-dimethylphenyl, ethylphenyl, propylphenyl, isopropylphenyl, t-butylphenyl or di-t-butylphenyl. Tolyl is preferred.

Halogen $R_3$ is, for example, chlorine or bromine, especially chlorine.

Those compositions are preferred which contain an elastomer and at least one compound of the formulae I or/and II.

Compositions containing a lubricant and at least one compound of the formulae I or/and II, wherein $R_2$ is methyl, ethyl or branched $C_3$-$C_{20}$-alkyl, allyl, methylallyl, propargyl or benzyl and $R_1$, $R_3$, $Z_1$ and $Z_2$ are as defined above, are also preferred.

Those compositions are of particular interest which contain an elastomer or a lubricant and at least one compound of the formula I or/and II, wherein the radicals $R_1$ are identical or different and independently of one another are $C_8$-$C_{20}$-alkyl or $C_1$-$C_4$-alkylene- COOR$_2'$, R$_2$ and R$_2'$ being C$_1$–C$_{20}$-alkyl, Z$_1$ is —CH$_2$— or —C(CH$_3$)$_2$— and Z$_2$ is as defined above.

Those compositions are particularly preferred which contain an elastomer or a lubricant and at least one compound of the formula I, wherein the radicals R$_1$ independently of one another are unsubstituted C$_8$–C$_{20}$-alkyl groups or are C$_1$–C$_{20}$-alkyl groups which are substituted by 1 or 2 hydroxyl groups, and those compositions are very particularly preferred in which the radicals R$_1$ are identical and especially are C$_8$–C$_{12}$-alkyl groups.

Those compositions are of particular importance which contain an elastomer or a lubricant and at least one compound of the formula IIa

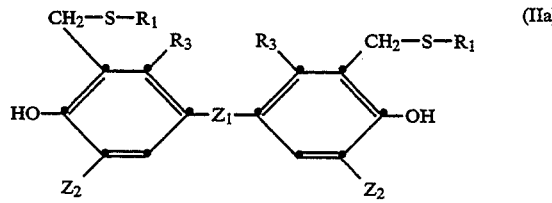

in which R$_1$, R$_3$, Z$_1$ and Z$_2$ are as defined above, and especially those compositions in which R$_3$ is hydrogen and Z$_1$ is —C(Z$_3$)(Z$_4$)—, Z$_3$ and Z$_4$ being as defined above.

Those compositions are very particularly preferred which contain a compound of the formula IIa, in which Z$_2$ is the —CH$_2$—S—R$_1$ radical.

The substances listed below are to be regarded as representative examples of compounds of the formulae I and II, which can be present in the compositions according to the invention: 2,6-bis-(2'-hydroxyethylthiomethyl)-4-methylphenol, 2,6-bis-(2',3'-dihydroxypropylthiomethyl)-4-methylphenol, 2,6-bis-(2'-methylaminocarbonylethylthiomethyl)-4-phenyl-phenol, 2,6-bis-(N,N-diethylaminocarbonyl-ethylthiomethyl)-4-allyl-phenol, 2,6-bis-(n-octylthiomethyl)-4-methylphenol, 2,6-bis-(t-octylthiomethyl)-4-t-butyl-phenol[1], 2,6-bis-(t-dodecylthiomethyl-4-t-octyl-phenol[2], 2,6-bis-(benzylthiomethyl)-6-methylphenol, 2,6-bis-(phenylthiomethyl)-4-t-butyl-phenol, 2,6-bis-(2'-ethylhexyloxycarbonylmethyl-thiomethyl )-4-cyclohexyl-phenol, 2,6-bis-(n-octadecyloxycarbonyl-methyl-thiomethyl)-4-propargyl-phenol, 2,6-bis-[2'-(2''-ethylhexyloxycarbonyl)-ethylthiomethyl]-4-t-butyl-phenol, 2,2-bis-[4',4''-dihydroxy-3',3'',5',5''-tetrakis-(octylthiomethyl)-phenol]-propane, 2,2-bis-]4',4''-dihydroxy-3',3'',5',5''-tetrakis-(dodecylthiomethyl)-phenyl]-methane and bis-[4',4''-dihydroxy-3',3'',5',5''-tetrakis-(2-ethylhexyloxycarbonylmethylthiomethyl)-phenyl] thioether.

[1] t-Octyl is 1,1,3,3-tetramethylbutyl
[2] t-Dodecyl is a mixture of 1,1,3,3,5,5-hexamethylhexyl and 1,1,4,6,6-pentamethylhept-4-yl As elastomer, the compositions according to the invention can contain, for example, the following materials:

1. Polydienes, for example polybutadiene, polyisoprene or polychloroprene; block polymers, for example styrene/butadiene/styrene, styrene/isoprene/styrene or acrylonitrile/butadiene copolymers.
2. Copolymers of monoolefins and diolefins with one another or with other vinyl monomers, for example ethylene/alkyl acrylate copolymers, ethylene/alkyl methacrylate copolymers, ethylene/vinyl acetate copolymers, and terpolymers of ethylene with propylene and a diene such as hexadiene, dicyclopentadiene or ethylidenenorbornene.
3. Halogen-containing polymers, for example polychloroprene, chlorinated rubber, chlorinated or chlorosulfonated polyethylene, epichlorohydrin homopolymers and copolymers, chlorotrifluoroethylene copolymers, polymers of halogen-containing vinyl compounds, for example polyvinylidene chloride, polyvinylidene fluoride, and copolymers thereof, such as vinyl chloride/vinylidene chloride, vinyl chloride/vinyl acetate or vinylidene chloride/vinyl acetate. p1 4. Polyurethanes derived from polyethers, polyesters and polybutadiene having terminal hydroxyl groups on the one hand and aliphatic or aromatic polyisocyanates on the other hand, and their initial products.
5. Natural rubber.
6. Mixtures (polyblends) of the polymers listed above.
7. Aqueous emulsions of natural or synthetic rubbers, for example natural rubber latex or latices of carboxylated styrene/butadiene copolymers.

In some cases, these elastomers are in the form of latices and can be stabilized as such.

Those compositions are preferred which contain, as the elastomer, a polydiene such as polybutadiene rubber, a halogen-containing polymer such as polyvinylidene fluoride or a polyurethane.

Advantageously, the compositions according to the invention contain 0.01–10% by weight of compounds of the formulae I or/and II as stabilizers, relative to the elastomer or to the lubricant, especially 0.05–5.0% by weight. Mixtures of these compounds can also be used.

Incorporation into the elastomers can be carried out, for example, by mixing in the substances of the formulae I or/and II, and if appropriate, further additives by the methods customary in industry, before or during shaping, or by applying the dissolved or dispersed compounds to the polymer, if appropriate with subsequent evaporation of the solvent. The compounds of the formulae I or II can also be added in the form of a master batch, which contains these compounds, for example, in a concentration from 2.5 to 25% by weight, to the plastics to be stabilized.

The elastomer-containing compositions according to the invention can be used in the most diverse forms, for example as sheets and films, fibres, tapes, moulding compositions, profiles or as binders for surface coatings, adhesives or cements.

In practice, the elastomer-containing compositions according to the invention can contain further additives, examples of these are:

1. Antioxidants 1.1 Alkylated monophenols, for example 2,6-di-t-butyl-4-methylphenol, 2-t-butyl-4,6-dimethylphenol, 2,6-di-t-butyl-4-ethylphenol, 2,6-di-t-butyl-4-n-butylphenol, 2,6-di-t-butyl-4-isobutylphenol, 2,6di-cyclopentyl-4-methylphenol, 2-(α-methylcyclohexyl)-4,6-dimethylphenol, 2,6-dioctadecyl-4-methylphenol, 2,4,6-tricyclohexylphenol and 2,6-di-t-butyl-4-methoxymethylphenol.

1.2. Alkylated hydroquinones, for example 2,6-di-t-butyl-4-methoxyphenol, 2,5-di-t-butylhydroquinone, 2,5-di-t-amylhydroquinone and 2,6-diphenyl-4-octadecyloxyphenol.

1.3. Hydroxylated thiodiphenyl ethers, for example 2,2'-thio-bis-(6-t-butyl-4-methylphenol), 2,2'-thio-bis-(4- octylphenol), 4,4'-thio-bis-(6-t-butyl-3-methylphenol) and 4,4'-thio-bis-(6-t-butyl-2-methylphenol).

1.4. Alkylidene-bisphenols, for example 2,2'-methylene-bis-(6-t-butyl-4-methylphenol), 2,2'-methylene-bis-(6-t-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-t-butylphenol), 2,2'-ethylidene-bis-(4,6-di-t-butylphenol), 2,2'-ethylidene-bis-(6-t-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-t-butylphenol), 4,4'-methylene-bis-(6-t-butyl-2-methylphenol), 1,1-bis-(5-t-butyl-4-hydroxy-2-methylphenyl)-butane, 2,6-bis-(3-t-butyl-5-methyl-2-hydroxybenzyl)-4-methylphenol, 1,1,3-tris-(5-t-butyl-4-hydroxy-2-methylphenyl)-butane, 1,1-bis-(5-t-butyl-4-hydroxy-2-methylphenyl)-3-n-dodecylmercaptobutane, ethylene glycol-bis-[3,3-bis-(3'-t-butyl-4'-hydroxyphenyl)butyrate], bis-(3-t-butyl-4-hydroxy-5-methylphenyl)-dicyclopentadiene and bis-[2-(3'-t-butyl-2'-hydroxy-5'-methylbenzyl)-6-t-butyl-4-methylphenyl] terephthalate.

1.5. Benzyl compounds, for example 1,3,5-tris-(3,5-di-t-butyl-4-hydroxybenzyl)-2,4,6-trimethylbenzene, bis-(3,5-di-t-butyl-4-hydroxybenzyl) sulfide, isooctyl 3,5-di-t-butyl-4-hydroxybenzyl-mercaptoacetate, bis-(4-t-butyl-3-hydroxy-2,6-dimethylbenzyl) dithiolterephthalate, 1,3,5-tris-(3,5-di-t-butyl-4-hydroxybenzyl) isocyanurate, 1,3,5-tris-(4-t-butyl-3-hydroxy-2,6-dimethylbenzyl) isocyanurate, dioctadecyl 3,5-di-t-butyl-4-hydroxybenzylphosphonate and calcium monoethyl 3,5-di-t-butyl-4-hydroxybenzylphosphonate.

1.6. Acylaminophenols, for example lauric acid 4-hydroxyanilide, stearic acid 4-hydroxyanilide, 2,4-bis-octylmercapto-6-(3,5-di-t-butyl-4-hydroxyanilino)-s-triazine and octyl N-(3,5-di-t-butyl-4-hydroxyphenyl)-carbonate.

1.7. Esters of β-(3,5-di-t-butyl-4-hydroxyphenyl)-propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxyethyl) isocyanurate and di-hydroxyethyl-oxamide.

1.8. Esters of β-(5-t-butyl-4-hydroxy-3-methylphenyl)-propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxyethyl) isocyanurate and di-hydroxyethyl-oxamide.

1.9. Amides of β-(3,5-di-t-butyl-4-hydroxyphenyl)-propionic acid, for example N,N'-bis-(3,5-di-t-butyl-4-hydroxyphenylpropionyl)-hexamethylenediamine, N,N'-bis-(3,5-di-t-butyl-4-hydroxyphenylpropionyl)-trimethylenediamine and N,N'-bis-(3,5-di-t-butyl-4-hydroxyphenylpropionyl)-hydrazine.

2. UV absorbers and light stabilizers 2.1. 2-(2'-Hydroxyphenyl)-benzotriazoles, for example the 5'-methyl, 3',5'-di-t-butyl, 5'-t-butyl, 5'-(1,1,3,3-tetramethylbutyl), 5-chloro-3',5'-di-t-butyl, 5-chloro-3'-t-butyl-5'-methyl, 3'-sec.-butyl-5'-t-butyl, 4'-octoxy, 3',5'-di-t-amyl and 3',5'-bis-(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of various substituted benzoic acids, for example 4-t-butylphenyl salicylate, phenyl salicylate, octylphenyl salicylate, dibenzoylresorcinol, bis-(4-t-butylbenzoyl)-resorcinol, benzoylresorcinol, 2,4-di-t-butylphenyl 3,5-di-t-butyl-4-hydroxybenzoate and hexadecyl 3,5-di-t-butyl-4-hydroxybenzoate.

2.4. Acrylates, for example ethyl α-cyano-β,β-diphenylacrylate, isoocty α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carboxymethoxy-β-cyanovinyl)-2-methylindoline.

2.5. Nickel compounds, for example nickel complexes of 2,2'-thio-bis-[4-(1,1,3,3-tetramethylbutyl)-phenol], such as the 1:1 or 1:2 complexes, which may contain additional ligands such as n-butylamine, triethanolamine or N-cyclohexyl-diethanolamine, nickel dibutyldithiocarbamate, nickel salts of the monoalkyl esters of 4-hydroxy-3,5-di-t-butyl-benzylphosphonic acid, such as the methyl or ethyl esters, nickel complexes of ketoximes such as 2-hydroxy-4-methyl-phenyl undecyl ketoxime and nickel complexes of 1-phenyl-4-lauroyl-4-hydroxy-pyrazole, with or without additional ligands.

2.6. Sterically hindered amines, for example bis-(2,2,6,6-tetramethylpiperidyl) sebacate, bis-(1,2,2,6,6-pentamethylpiperidyl) sebacate, bis-(1,2,2,6,6-pentamethylpiperidyl) n-butyl-3,5-di-t-butyl-4-hydroxybenzylmalonate, the condensation product of 1-hydroxyethyl-2,2,6,6-tetramethyl-4-hydroxypiperidine and succinic acid, the condensation product of N,N'-bis-(2,2,6,6-tetramethyl-4-piperidyl)-hexamethylenediamine and 4-t-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl) 1,2,3,4-butanetetracarboxylate and 1,1'-(1,2-ethanediyl)-bis-(3,3,5,5-tetramethylpiperazinone).

2.7. Oxalic acid diamides, for example 4,4'-dioctyloxyoxanilide, 2',2-dioctyloxy-5,5'-di-t-butyloxanilide, 2,2'-didodecyloxy-5,5'-di-t-butyloxanilide, 2-ethoxy-2'-ethyloxanilide, N,N'-bis-(3-dimethylaminopropyl)-oxamide, 2-ethoxy-5-t-butyl-2'-ethyl-oxanilide and its mixtures with 2-ethoxy-2'-ethyl-5,4'-di-t-butyloxanilide, and mixtures of o- and p-methoxy- and o- and p-ethoxy-disubstituted oxanilides.

3. Metal deactivators, for example N,N'-diphenyloxamide, N-salicylal-N'-salicyloylhydrazine, N,N'-bis-salicyloylhydrazine, N,N'-bis-(3,5-di-t-butyl-4-hydroxyphenylpropionyl)-hydrazine, 3-salicyloylamino-1,2,4-triazole and bis-benzylidene-oxalodihydrazide.

4. Phosphites and phosphonites, for example triphenyl phosphite, diphenyl alkyl phosphites, phenyl dialkyl phosphites, tris-(nonylphenyl) phosphite, trilauryl phosphite, trioctadecyl phosphite, distearyl pentaerythritol diphosphite, tris-(2,4-di-t-butylphenyl) phosphite, diisodecyl pentaerythritol diphosphite, bis-(2,4-di-t-butylphenyl) pentaerythritol diphosphite, tristearyl sorbitol triphosphite, tetrakis-(2,4-di-t-butylphenyl) 4,4'-diphenylene-diphosphonite and 3,9-bis-(2,4-di-t-butylphenoxy)-2,4,8,10-tetraoxa-3,9-diphosphaspiro[5.5]undecane.

5. Peroxide-destroying compounds, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide and pentaerythritol tetrakis-(β-dodecylmercapto)-propionate.

6. Polyamide stabilizers, for example copper salts in combination with iodides and/or phosphorus compounds and divalent manganese salts.

7. Basic costabilizers, for example melamine, polyvinylpyrrolidone, triallyl cyanurate, urea derivatives, hydrazine derivatives, amines, polyamides, polyurethanes, alkali metal or alkaline earth metal salts of higher fatty acids, for example calcium stearate, zinc stearate, magnesium stearate, sodium ricinoleate and potassium palmitate, antimony pyrocatecholate or zinc pyrocatecholate.

8. Nucleating agents, for example 4-t-butylbenzoic acid, adipic acid and diphenylacetic acid.

9. Fillers and reinforcing agents, for example calcium carbonate, silicates, glass fibres, asbestos, talc, kaolin, mica, barium sulfate, metal oxides and hydroxides, carbon black and graphite.

10. Further additives, for example plasticizers, lubricants, emulsifiers, pigments, fluorescent brighteners, flameproofing agents, antistatic agents, blowing agents, waxes, oils or organic solvents.

As lubricants, the compositions according to the invention can contain lubricants based on mineral oils or synthetic oils.

The appropriate lubricants are known to those skilled in the art and are described, for example, in "Schmiermittel Taschenbuch [Lubricants Handbook]" (Hüthig Verlag, Heidelberg, 1974).

Lubricant formulations according to the invention can, moreover, also contain further additives, which are added in order to improve certain use properties, for example further antioxidants, metal passivators, rust inhibitors, viscosity index improvers, pour point depressants, dispersants/surfactants and anti-wear additives.

Examples of antioxidants can be taken from the list given above under item 1 for elastomer-containing compositions.

Examples of further additives for the lubricant compositions according to the invention are:

Examples of amine-type antioxidants: N,N'-di-isopropyl-p-phenylenediamine, N,N'-di-sec-butyl-p-phenylenediamine, N,N'-bis-(1,4-dimethyl-phenyl)-p-phenylenediamine, N,N'-bis-(1-ethyl-3-methyl-pentyl)-p-phenylenediamine, N,N'-bis-(1-methyl-heptyl)-p-phenylenediamine, N,N'-diphenyl-p-phenylenediamine, N,N'-di-(2-naphthyl)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, diphenylamine, 4-isopropoxydiphenylamine, N-phenyl-1-naphthylamine, N-phenyl-2-naphthylamine, octylated diphenylamine, 4-n-butylaminophenol, 4-butyrylamino-phenol, 4-nonanoylamino-phenol, 4-dodecanoylamino-phenol, 4-octadecanoylamino-phenol, di-(4-methoxy-phenyl)-amine, 2,6-di-tert-butyl-4-dimethylamino-methylphenol, 2,4'-diamino-diphenylmethane, 4,4'-diamino-diphenylmethane, N,N,N',N'-tetramethyl-4,4'-diamino-diphenylmethane, 1,2-di-[(2-methylphenyl)-amino]-ethane, 1,2-di-(phenylamino)-propane, (o-tolyl)-biguanide, di-[4-(1',3'-dimethyl-butyl)-phenyl]-amine, tert-octylated N-phenyl-1-naphthylamine and a mixture of mono- and di-alkylated tert-butyl-/tert-octyl-diphenylamines.

Examples of metal passivators are: for copper, for example: triazole, benzotriazole and derivatives of these, 2-mercaptobenzothiazole, 2,5-dimercapto-thiadiazole, salicylidene-propylenediamine and salts of salicylaminoguanidine.

Examples of rust inhibitors are:
a) organic acids, their esters, metal salts and anhydrides, for example: N-oleoyl-sarcosine, sorbitan monooleate, lead naphthenate, dodecenylsuccinic anhydride, alkenylsuccinic acid half esters and 4-nonylphenoxyacetic acid.
b) Nitrogen-containing compounds, for example:
I. primary, secondary or tertiary aliphatic or cycloaliphatic amines and amine salts of organic and inorganic acids, for example oil-soluble alkyl ammonium carboxylates.
II. Heterocyclic compounds, for example: substituted imidazolines and oxazolines.
c) Phosphorus-containing compounds, for example: amine salts of phosphoric acid partial esters.
d) Sulfur-containing compounds, for example: barium dinonylnaphthalenesulfonates and calcium petroleum-sulfonates.

Examples of viscosity index improvers are:
polymethacrylates, vinylpyrrolidone/methacrylate copolymers, polybutenes, olefin copolymers and styrene/acrylate copolymers.

Examples of pour point depressants are:
polymethacrylate and alkylated naphthalene derivatives.

Examples of dispersants/surfactants are:
polybutenylsuccinic acid imides, polybutenylphosphonic acid derivatives and basic magnesium, calcium and barium sulfonates and phenolates.

Examples of anti-wear additives are:
compounds containing sulfur and/or phosphorus and/or halogen, such as sulfurated vegetable oils, zinc dialkyl dithiophosphates, tritolyl phosphate, chlorinated paraffins and alkyl and aryl disulfides.

Some compounds of the formula I are known. Those compounds of formula I which are novel and the compounds of the formula II are also subjects of the present invention.

The invention therefore also relates to compounds of the formulae Ia or II

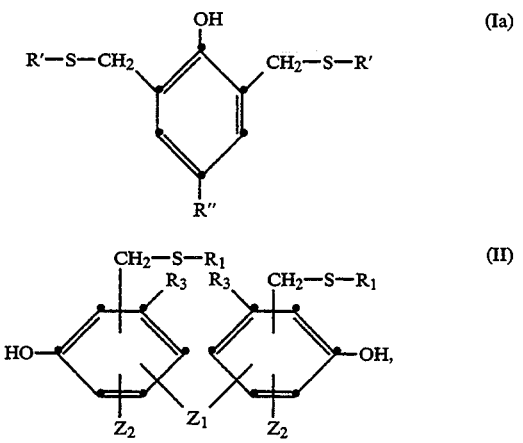

in which the radicals R' are identical or different and independently of one another are $C_8$–$C_{20}$-alkyl or $C_1$–$C_{20}$-alkyl which is substituted by 1 or 2 hydroxyl groups or/and interrupted by —O—, or are $C_1$–$C_4$-alkylene-CO—NR$_2''$R$_4$, $C_5$–$C_{12}$-cycloalkyl, 1-naphthyl, 2-naphthyl, $C_1$–$C_4$-alkylphenyl, α-methylbenzyl or α,α- dimethylbenzyl, R" is methyl, ethyl or branched $c_3$-$C_{20}$-alkyl, allyl, methallyl, propargyl or benzyl and $R_1$, $R_2''$, $R_3$, $R_4$, $Z_1$ and $Z_2$ are as defined above, with the proviso that the phenols of the formula II are free of the —$CH_2$—S—$R_1$ functional group in the m-position relative to the OH group.

The possible definitions of $R_1$ and $R_2$ in the formula I, as already given above as examples and as being preferred, analogously apply also to R' and R" in the formula Ia. The same applies to the symbols $R_1$, $R_2'$, $R_3$, $R_4$, $Z_1$ and $Z_2$.

Those compounds of the formula Ia are preferred in which the radicals R' are identical and, in particular, are $C_8$-$C_{20}$-alkyl.

Those compounds of formula Ia are also preferred in which R" is methyl, ethyl or branched $C_3$-$C_{20}$-alkyl. Moreover, those compounds of the formula II are preferred which are of the formula IIa

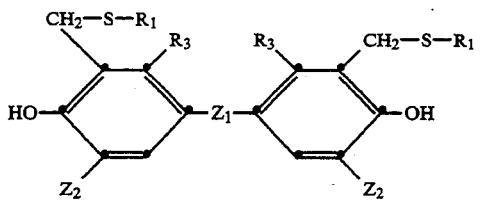

(IIa)

in which $R_1$, $R_3$, $Z_1$ and $Z_2$ are as defined above.

Those compounds of the formula IIa are particularly preferred in which $R_3$ is hydrogen and $Z_1$ is —C($Z_3$)($Z_4$)—, $Z_3$ and $Z_4$ being as defined above. Those compounds are very particularly preferred in which $Z_2$ is the radical —$CH_2$—S—$R_1$.

The known compounds and novel compounds of the formulae I, Ia and II are prepared by methods known per se, such as are described, for example, in EP-A-0,165,209 and in U.S. Pat. No. 3,227,677. However, they can also be obtained by reacting a phenol of the formulae III or IV

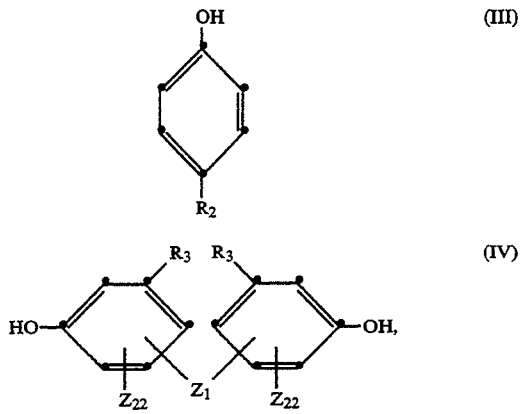

(III)

(IV)

in which $R_2$, $R_3$ and $Z_1$ are as defined above and $Z_{22}$ is hydrogen or $C_1$-$C_{20}$-alkyl, with formaldehyde or a compound which releases formaldehyde under the reaction conditions, and with at least one mercaptan $R_1$—SH in the presence of a base, the base being mono-, di- or tri-methylamine or mono- or di-ethylamine.

Preferably, mono- or di-methylamine and especially dimethylamine are used. The base can be used, for example, in the form of a 10–35% solution in ethanol, methanol or other lower alcohols, or in the pure form. Dimethylamine can also be used as a gas. The base can be employed, for example, in a quantity of 1–50 mol %, preferably 2–30 mol %, and especially 5–20%, relative to the mercaptan.

The reaction can be carried out in the presence of a solvent.

Examples of suitable solvents are alcohols having 1 to 6 carbon atoms, for example methanol, ethanol, propanol, butanol, pentanol or hexanol. However, diols, polyols and ethers thereof can also be used, for example glycol, glycerol and polyethylene glycol. The reaction can also be carried out in polar aprotic solvents, for example dimethylformamide or dimethyl sulfoxide, or high-boiling aromatic or aliphatic hydrocarbons, which may be chlorinated, can be employed, for example toluene, ligroin or chlorobenzene. Preferably, dimethylformamide is used which, if appropriate, is diluted with one of the abovementioned lower alcohols or chlorinated hydrocarbons.

Examples of compounds which form formaldehyde under the reaction conditions are paraformaldehyde or hexamethylenetetramine.

The reactants phenol, formaldehyde and mercaptan can be employed in stoichiometric amounts. Sometimes, however, it can be of advantage to employ an excess of formaldehyde and/or mercaptan. Mixtures of phenols and/or mercaptans can also be reacted.

The process can be carried out advantageously at temperatures of 80°–160° C., preferably 90°–150° C. and especially 90°–130° C. and, if appropriate, under pressure (for example 0.01 to 5 bar). In the absence of a solvent, the reaction is preferably carried out under pressure.

The reaction times can vary depending on the specific phenol and mercaptan and are, for example, 1 to 24 hours, in particular 1 to 6 hours. Advantageously, the reaction mixture is heated under reflux in a nitrogen atmosphere.

All the starting products are known compounds and can be prepared by known processes. Some of them are also commercially available.

The examples which follow illustrate the invention in more detail.

PREPARATION EXAMPLES

EXAMPLE 1

Preparation of 2,6-bis-(n-octylthiomethyl)-4-t-butylphenol

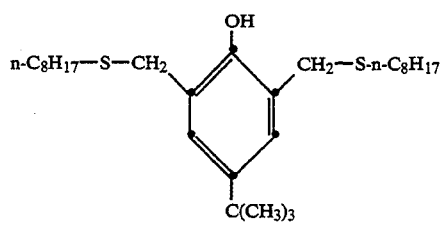

A mixture of 22.5 g of 4-t-butylphenol, 18.0 g of paraformaldehyde, 43.9 g of n-octanethiol, 4.0 g of 33% ethanolic dimethylamine and 23 ml of N,N-dimethylformamide is heated under nitrogen for 3 hours under reflux in a sulfonation flask with a reflux condenser and mechanical stirrer. The internal temperature is 110° C.

The crude product is taken up in 150 ml of ethyl acetate and washed with 100 ml of water. After evaporation of the organic phase to dryness, this gives 51 g (97% of theory) of 2,6-bis-(n-octylthiomethyl)-4-t-butylphenol as a colourless oil.

Analytical figures: Calculated: 13.74% S Found: 13.44% S.

EXAMPLE 2

Preparation of 2,6-bis-(n-octylthiomethyl)-4-(1',1',3',3'-tetramethylbutyl)-phenol

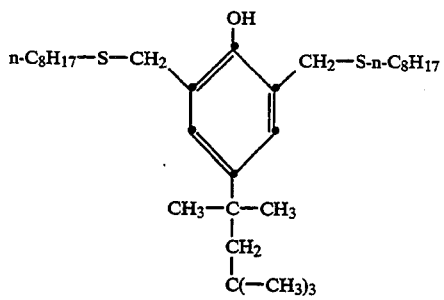

The procedure followed is as in Example 1, but using 0.1 mol of 4-(1',1',3',3'-tetramethylbutyl)-phenol in place of 4-t-butylphenol. This gives 43.6 g (83% of theory) of the product as a colourless oil.

Analytical figures: Calculated: 12.26% S Found: 12.28% S

EXAMPLE 3

Preparation of 2,2-bis-[4',4''-dihydroxy-3',3'',5',5''-tetrakis-(n-octylthiomethyl)-phenyl]-propane

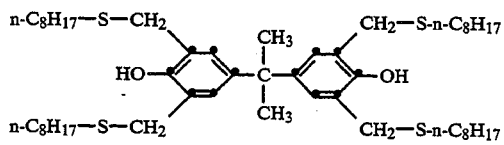

The procedure followed is as in Example 1, but using the following mixture: 23.2 g of bisphenol A, 20.4 g of paraformaldehyde, 60.33 g of n-octanethiol, 7.5 g of 33% ethanolic dimethylamine and 40 ml (38 g) of N,N-dimethylformamide. The reaction time is 6 hours. The crude product is taken up in methylene chloride and washed with water. This gives 86 g (99% of theory) of the product as a slightly yellowish oil.

Analytical figures: Calculated: 14.89% S Found: 14.87% S

EXAMPLE 4

Preparation of 2,2-bis-[4',4''-dihydroxy-3',3'',5',5''-tetrakis-(n-dodecylthiomethyl)-phenyl]-propane

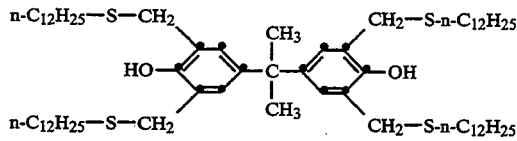

The procedure followed is as in Example 3, but using an equivalent quantity (in mol) of n-dodecanethiol in place of n-octanethiol. This gives 108.9 g (99% of theory) of the product as a yellowish oil.

Analytical figures: Calculated: 11.81% S Found: 11.67% S.

EXAMPLE 5

Preparation of a mixture of the formula

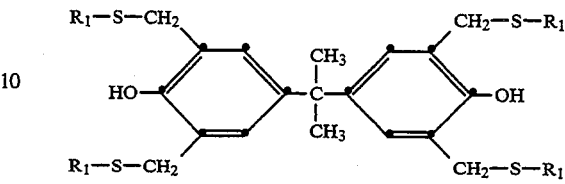

in which $R_1$ is n-octyl and/or n-dodecyl.

The procedure followed is as in Example 3, but using a 1:1 mixture of 0.2 mol of n-octanethiol and 0.2 mol of n-dodecanethiol in place of 0.4 mol of n-octanethiol.

This gives 97.9 g of a slightly yellowish oil. After chromatographic purification, this gives a yellowish oil which has a flowery odour and which, according to HPLC analysis (High Pressure Liquid Chromatography) is a statistical mixture of 2,2-bis-[4',4''-dihydroxy-3',3,5',5''-tetrakis-($R_1$-thiomethyl)-phenyl]-propanes, $R_1$ being n-octyl or n-dodecyl.

Analytical figures: (for 2×octyl+2×dodecyl) Calculated: 13.17% S Found: 13.21% S.

EXAMPLE 6

Preparation of bis-[4,4'-dihydroxy-3,3',5 5'-tetrakis-(n-octylthiomethyl)-phenyl]-methane

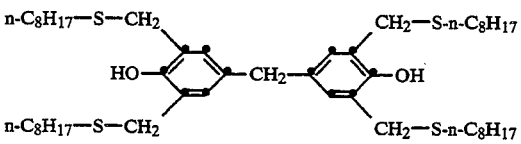

The procedure followed is as in Example 3, but using the equivalent quantity (in mol) of bisphenol F in place of bisphenol A. After extraction with hexane, this gives 76.7 g of an orange-coloured oil. According to $^1$H-NMR spectroscopy (100 MHz, CDCl$_3$), this contains, in addition to the named product, also corresponding reaction products of o,p- and o,o-isomers of bisphenol F as impurities.

Analytical figures: Calculated: 15.39% S Found: 15.28% S.

EXAMPLE 7

Preparation of bis-[4,4'-dihydroxy-3,3',5,5'-tetrakis-(n-dodecylthiomethyl)-phenyl]-methane

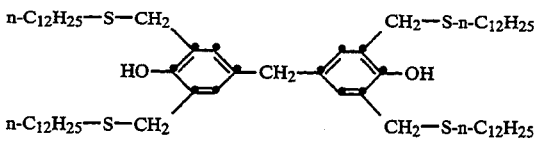

The procedure followed is as in Example 6, except that the equivalent quantity (in mol) of n-dodecanethiol is used in place of n-octanethiol. This gives a reddish oil (yield: 93%) which crystallizes in the cold. Melting point 40°–42° C. This time again, the end product contains, in addition to the named main product, also reaction products of o,p- and o,o-isomers of bisphenol F as impurities.

Analytical figures: Calculated: 12.12% S Found: 12.01% S.

EXAMPLE 8:

Preparation of 2,2-bis-[4',4''-dihydroxy-3',3'',5',5''-tetrakis-(n-octylthiomethyl)-phenyl]-propane

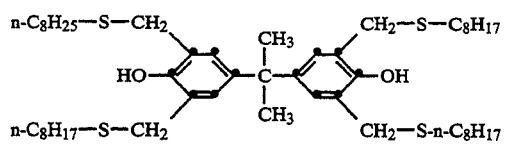

a) 23.3 g of bisphenol A, 52 g of 40% aqueous dimethylamine solution and 43.4 g of 36% aqueous formaldehyde solution are heated for 18 hours at 75° C. After usual working-up by extraction and drying as well as recrystallization from ligroin, this gives 2,2-bis-[4',4''-dihydroxy-3',3'',5',5''-tetrakis-(N,N-dimethylaminoethyl)-phenyl]-propane as a colourless powder, melting point 91°–93° C. (yield: 94%).

b) 10.72 g of the product obtained under a), 15.1 g of n-octanethiol and 0.75 g of powdered potassium hydroxide are heated at 90° C. until a clear solution has formed. At room temperature, 5 ml of N,N-dimethylformamide are added and the mixture is then heated under nitrogen for 7 hours at 120° C. internal temperature.

After usual working-up, this gives 2,2-bis-[4',4''-dihydroxy-3',3'',5',5''-tetrakis-(n-octylthiomethyl)-phenyl]-propane as a slightly yellowish oil (yield: 92.1%).

Analytical figures: Calculated: 14.89% S Found: 15.07% S

EXAMPLE 9

Preparation of 2,6-bis-(n-octylthiomethyl)-4-t-butyl-phenol

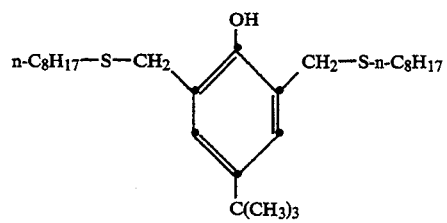

a) 177.7 g of 4-t-butylphenol, 350 ml of 95% ethanol, 266.6 g of 40% aqueous dimethylamine solution and 199.1 g of 36% aqueous formaldehyde solution are heated under reflux for 12 hours. Fractional distillation gives 280 g (85% of theory) of 2,6-bis-(N,N-dimethylaminomethyl)-4-t-butylphenol as a yellow oil, boiling point 103° C. (at 13.3 Pa).

b) 39.6 g of the compound obtained under a) are heated with 43.9 g of n-octanethiol for 24 hours at 150° C. under a slight vacuum of about 0.53 bar. After purification by column chromatography, this gives 2,6-bis-(n-octylthiomethyl)-4-t-butylphenol as a yellowish oil (yield: 69.9 g=98%).

Analytical figures: Calculated: 13.73% S Found: 13.92% S.

EXAMPLE 10

Preparation of 2,2-bis-[4',4''-dihydroxy-3',3'',5',5''-tetrakis-(2'''ethylhexyloxycarbonyl-methylthiomethyl)-phenyl]-propane

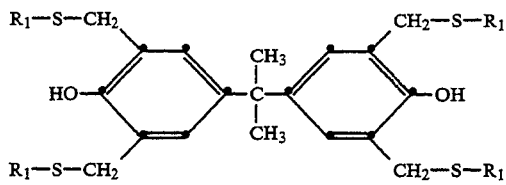

$R_1 = -CH_2-COO-CH_2-CH(CH_2CH_3)-(CH_2)_3-CH_3$

The procedure followed is as in Example 3, but using the equivalent quantity (in mol) of 2-ethylhexyl thioglycolate in place of n-octanethiol. This gives the product as a yellowish oil (yield: 93.4%).

Analytical figures: Calculated: 11.73% S Found: 11.45% S

EXAMPLE 11

Preparation of 2,6-bis-(n-octylthiomethyl)-4-methylphenol

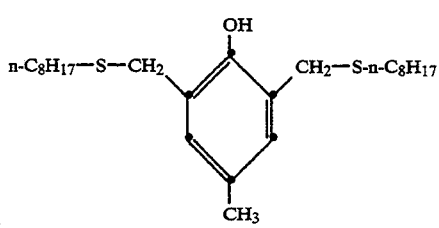

The procedure followed is as in Example 1, but using the equivalent quantity (in mol) of p-cresol in place of 4-t-butylphenol. This gives the product as a yellowish oil (yield: 99.3%).

Analytical figures: Calculated: 15.10% S Found: 15.03% S

EXAMPLE 12

Preparation of
2,6-bis-(2'-ethylhexyloxycarbonyl-methylthio-methyl)-
4-t-butylphenol

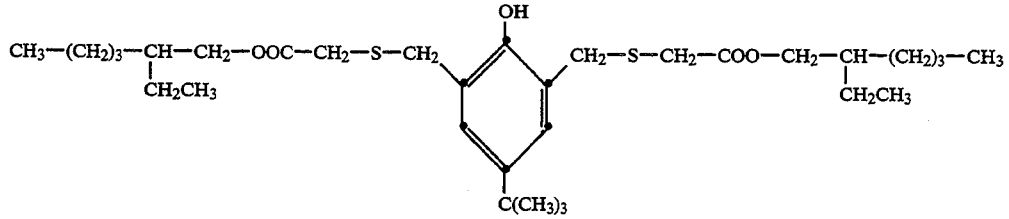

The procedure followed is as in Example 1, but using the equivalent amount (in mol) of 2-ethylhexyl thioglycolate. This gives the product as a yellowish oil (yield: 82.5%).

Analytical figures: Calculated: 11.0% S Found: 10.73% S

Table 1 which follows contains characteristic $^1$H-NMR spectroscopic data for Examples 1 to 12 (aryl-$CH_2$—S signal). The data are given in ppm and relate to the following structures:

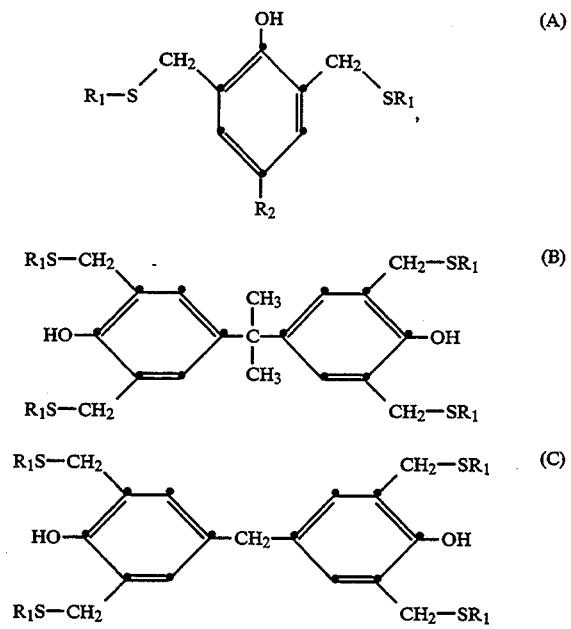

TABLE 1

| Example No. | Ar—$CH_2$S-** | Structure | $R_1$ | $R_2$ |
|---|---|---|---|---|
| 1 | 3.80 (s) | A | n-$C_8H_{17}$ | t-Butyl |
| 2 | 3.77 (s) | A | n-$C_8H_{17}$ | t-Octyl |
| 3 | 3.73 (s) | B | n-$C_8H_{17}$ | — |
| 4 | 3.73 (s) | B | n-$C_{12}H_{25}$ | — |
| 5 | 3.73 (s) | B | $C_{12}H_{25}/C_8H_{17}$ | — |
| 6 | 3.75 (s) | C | $C_8H_{17}$ | — |
| 7 | 3.75 (s) | C | $C_{12}H_{25}$ | — |
| 8 | 3.73 (s) | B | $C_8H_{17}$ | — |
| 9 | 3.80 (s) | A | n-$C_8H_{17}$ | t-Butyl |
| 10 | 3.86 (s) | B | $CH_2COO$-2-ethyl-hexyl | — |
| 11 | 3.78 (s) | A | n-$C_8H_{17}$ | $CH_3$ |
| 12 | 3.90 (a) | A | $CH_2COO$-2-ethyl-hexyl | t-Butyl |

*s = Singlet
**Ar—$CH_2$S = Aryl-$CH_2$-S signal

Application Example

Stabilization of polybutadiene rubber (oven ageing)

100 g of polybutadiene, prestabilized with 0.4% of 2,6-di-t-butyl-p-cresol, are mixed homogeneously for 6 minutes in a roll mill with 0.25% of 2,6-bis-(n-octylthiomethyl)-4-t-butylphenol from Example 1. The rolled hides are pressed at 80° C. to give 10 mm thick plates. A further plate is produced in the same way without stabilizer.

The compositions according to the invention are tested by heat-ageing in a circulating-air oven at 80° C. The criterion used is the undesired gel content which arises in the course of oven ageing. This is determined in the following way:

1 g of polybutadiene is dissolved overnight at room temperature in 100 ml of toluene. The solution is filtered through a glass suction filter (00 pore size), and the filtered solution is evaporated to dryness.

The gel content is obtained from $$Gel = \frac{E - A}{E} \times 100(\%)$$

E = weight taken (1 g)
A = weight of the evaporation residue

After an induction period, the gel content increases rapidly. The time after which gel content of 2% is reached is used as an arbitrary definition of the induction period. This induction time is determined by periodic determinations of the gel content.

The measurement shows that the sample which contains the compound from Example 1 takes an induction time of several weeks, as compared with the sample without stabilizer until the gel content reaches 2%.

What is claimed is:

1. A composition comprising a lubricant and at least one compound of the formulae I or/and II

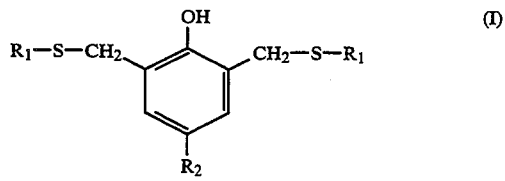

-continued

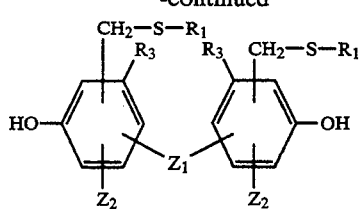

in which the radicals $R_1$ are identical or different and independently of one another are $C_8$–$C_{20}$-alkyl which is unsubstituted or substituted by 1 or 2 hydroxyl groups or/and interrupted by —O—, or are $C_1$–$C_4$-alkylene—COOR'$_2$, $C_1$–$C_4$-alkylene—CO—NR''$_2$R$_4$ or $C_5$–$C_{12}$-cycloalkyl, $R_2$, $R'_2$ and $R''_2$ independently of one another are $C_1$–$C_{20}$-alkyl, allyl, methallyl, propargyl, $C_5$–$C_{12}$-cycloalkyl, phenyl or benzyl, $R_3$ is hydrogen, $C_1$–$C_{20}$-alkyl, $C_2$–$C_{18}$-alkenyl or halogen, $R_4$ is hydrogen, $C_1$–$C_{20}$-alkyl or $C_2$–$C_{18}$-alkenyl, $Z_1$ is —S— or —C($Z_3$)($Z_4$)— and $Z_2$ is hydrogen, $C_1$–$C_{20}$-alkyl or —CH$_2$—S—R$_1$, $Z_3$ and $Z_4$ independently of one another being hydrogen or methyl, with the proviso that the phenols of the formula II are free of the —CH$_2$—S—R$_1$ functional group in the m-position relative to the OH group.

2. A composition according to claim 1, comprising a lubricant and at least one compound of the formulae I or II, in which $R_2$ is methyl, ethyl or branched $C_3$–$C_{20}$-alkyl, allyl, methallyl, propargyl or benzyl and $R_1$, $R_3$, $Z_1$ and $Z_2$ are as defined in claim 1.

3. A composition according to claim 1, comprising at least one compound of the formulae I or/and II, in which the radicals $R_1$ are identical or different and independently of one another are $C_8$–$C_{20}$-alkyl or $C_1$–$C_4$-alkylene—COOR$_2$', $R_2$ and $R_2$' are $C_1$–$C_{20}$-alkyl, $Z_1$ is —CH$_2$— or —C(CH$_3$)$_2$— and $Z_2$ is as defined in claim 1.

4. A composition according to claim 1, comprising at least one compound of the formula I, in which the radicals $R_1$ independently of one another are $C_8$–$C_{20}$-alkyl groups, which are unsubstituted, or $C_1$–$C_{20}$-alkyl groups, which are substituted by 1 or 2 hydroxyl groups.

5. A composition according to claim 1, wherein the radicals $R_1$ are identical and are $C_8$–$C_{12}$-alkyl groups.

6. A composition according to claim 1, comprising at least one compound of the formula IIa

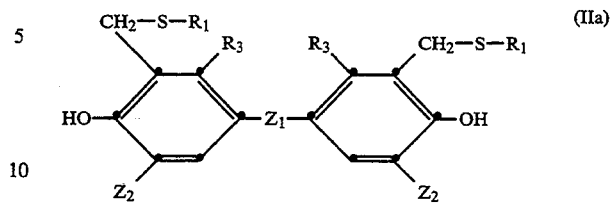

in which $R_1$, $R_3$, $Z_1$ and $Z_2$ are as defined in claim 1.

7. A composition according to claim 6, wherein $R_3$ is hydrogen and $Z_1$ is —C($Z_3$)($Z_4$)—.

8. A composition according to claim 6, wherein $Z_2$ is the radical —CH$_2$—S—R$_1$.

9. A composition according to claim 1, comprising 0.01–10.0% by weight of a compound of the formula I or/and II, relative to the lubricant.

10. A compound of formula IIa

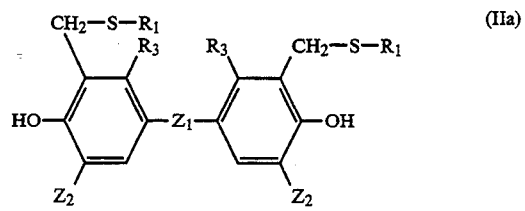

in which the radicals $R_1$ are identical or different and independently of one another are $C_1$–$C_{20}$-alkyl which is unsubstituted or substituted by 1 or 2 hydroxyl groups or/and interrupted by —O—, or are $C_1$–$C_4$-alkylene—COOR$_2$', $C_1$–$C_4$-alkylene—CO—NR$_2$''R$_4$, $C_5$–$C_{12}$-cycloalkyl, phenyl, 1-naphthyl, 2-naphthyl, $C_1$–$C_4$-alkyl-phenyl or phenyl-$C_1$–$C_4$-alkyl, $R_3$ is hydrogen, $C_1$–$C_{20}$-alkyl, $C_2$–$C_{18}$-alkenyl or halogen, $Z_1$ is —S— or —C($Z_3$)($Z_4$)— and $Z_2$ is hydrogen, $C_1$–$C_{20}$-alkyl or —CH$_2$—S—R$_1$, with the proviso that the phenols of the formula II are free of the —CH$_2$—S—R$_1$ functional group in the m-position relative to the OH group.

11. A compound according to claim 10, wherein $R_3$ is hydrogen and $Z_1$ is —C($Z_3$)($Z_4$)—.

12. A compound according to claim 10, wherein $Z_2$ is a —CH$_2$—S—R$_1$ radical.

* * * * *